United States Patent [19]

Mesek

[11] 4,282,874

[45] Aug. 11, 1981

[54] DISPOSABLE ABSORBENT ARTICLE OF MANUFACTURE

[75] Inventor: Frederick K. Mesek, Tinley Park, Ill.

[73] Assignee: Johnson & Johnson Baby Products Company, New Brunswick, N.J.

[21] Appl. No.: 38,370

[22] Filed: May 11, 1979

[51] Int. Cl.³ .............................................. A41B 13/02
[52] U.S. Cl. .................................................... 128/287
[58] Field of Search ............................... 128/155–156, 128/284, 287, 290

[56] References Cited

U.S. PATENT DOCUMENTS

| 2,923,298 | 2/1960 | Dockstader et al. | 128/290 R |
| 3,017,304 | 1/1962 | Burgeni | 128/290 R |
| 3,494,362 | 2/1970 | Burgeni | 128/290 R |
| 3,762,415 | 10/1973 | Morrison | 128/290 R |
| 3,965,906 | 6/1976 | Karami | 128/290 R |
| 4,014,341 | 3/1977 | Karami | 128/284 |
| 4,184,902 | 1/1980 | Karami | 128/287 |

Primary Examiner—C. Fred Rosenbaum
Attorney, Agent, or Firm—Martha A. Michaels

[57] ABSTRACT

The present invention provides an absorbent article including a multilayer absorbent pad. The pad contains a first highly-porous, loosely-compacted cellulosic fibrous batt, a moisture-impervious film having a plurality of openings therein and on the other side of the film a second batt of greater density than the first batt.

14 Claims, 5 Drawing Figures

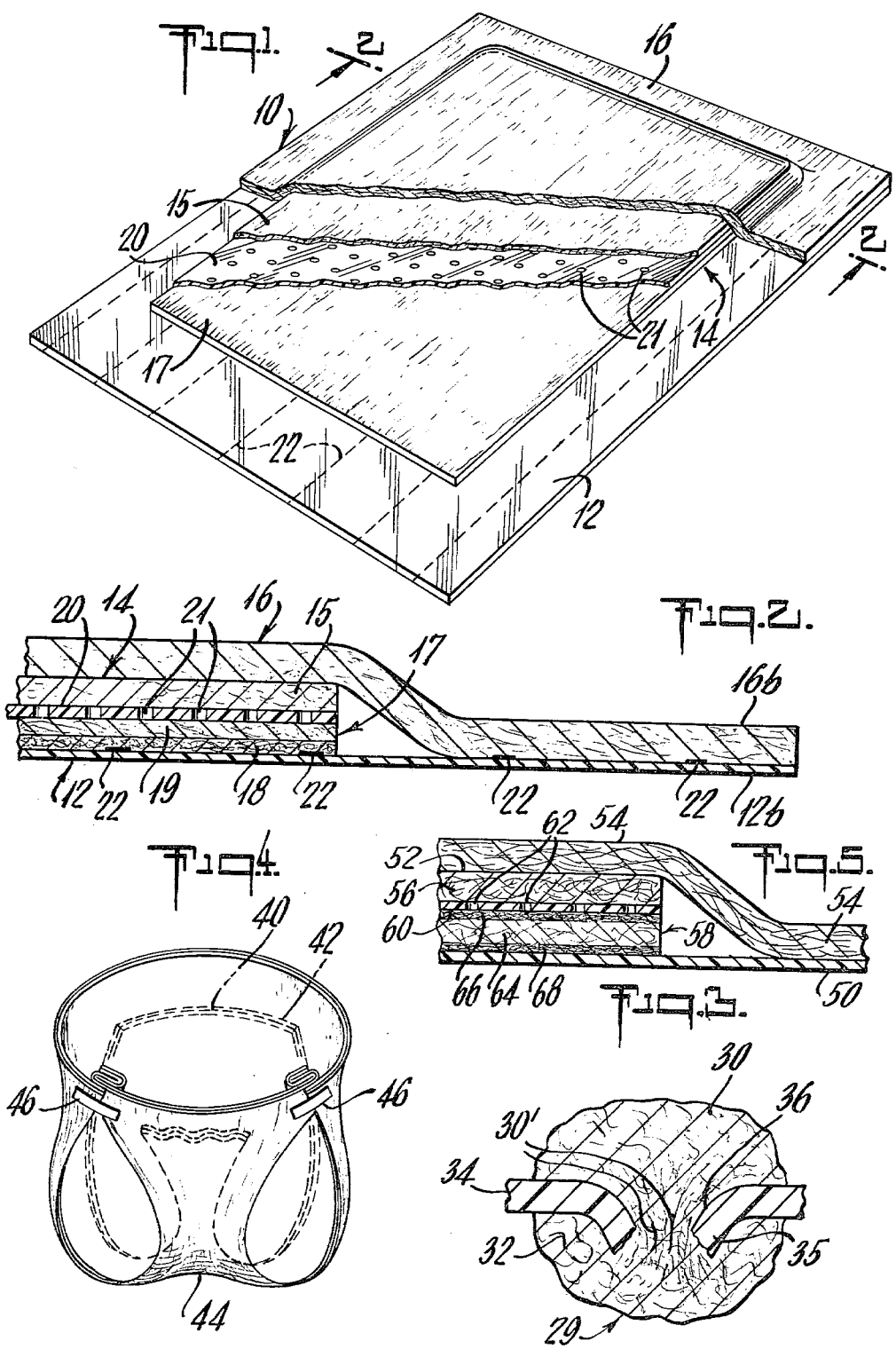

DISPOSABLE ABSORBENT ARTICLE OF MANUFACTURE

BACKGROUND OF THE INVENTION

The present invention relates to disposable absorbent articles such as disposable diapers, sanitary napkins, and the like.

Disposable diapers provide substantial advantages and convenience over diapers that have to be laundered and reused, particularly when the diapers are used away from home. In recent years, many different disposable diapers have been proposed and some have been successful in the marketplace. However, even the successful diapers may be inadequate in functioning properties, and their commercial success has come at least in part, because consumers have been willing to accept inadequate performance as part of the price for convenience.

One design criterion which has not heretofore been met adequately is keeping moisture away from the surface of the diaper which comes into contact with the infant's skin to thereby avoid skin irritation and infection, while at the same time handling a full volume discharge of urine.

One disposable diaper representing a significant advance in the art is a multilayer diaper comprising, in order, a fibrous facing layer which is to be brought into contact with the infant's skin, a layer of a highly porous, loosely compacted cellulosic batt, a paper-like densified, highly compacted cellulosic fibrous layer integral with the loosely compacted batt, and an impervious backing sheet adhered to the densified layer at the interface therebetween. The facing layer is of porous construction and its fibers have less wettability for water than the fibers of the loosely compacted batt, resulting in a tendency for liquid to flow from the facing layer into the batt. The densified fibrous layer has a smaller average pore size than the loosely compacted batt, resulting in a tendency for liquid to flow preferentially from the batt into the underlying densified layer rather than to other areas of the batt, thus tending to restrict wetting in the batt to an area of moderate size. Liquid flowing into the densified layer tends to spread laterally because of the wicking action of the densified layer and liquid which might pass through the densified layer during discharge is held back by the impervious backing sheet usually for a sufficient time to permit absorption to take place. Liquid in excess of the absorptive capacity of the densified layer is forced back by the impervious layer into the dry portion of the loosely compacted batt, thus utilizing the additional absorptive capacity therein.

However, while the diaper structure described above represents a significant advance in the art, particularly in its ability to maintain the layer in contact with an infant's skin dry, during periods of heavy discharge, after the densified layer and integral loosely compacted batt become saturated over a sufficient area, there is a tendency for urine to wet back into the facing layer.

SUMMARY OF THE INVENTION

The absorbent article disclosed herein represents a significant improvement over the structure disclosed above by providing a novel absorbent panel which permits urine to be readily absorbed in a portion of the panel that is remote from the facing layer, and which effectively traps the urine in the portion remote from the facing layer, so that urine cannot flow back and wick into the facing layer.

To achieve this important and desirable result, the absorbent article of the present invention includes a multilayer absorbent pad having a first highly-porous, loosely-compacted cellulosic fibrous batt, a moisture-impervious film having a plurality of openings therein on one side of the first batt and on the other side of the moisture-impervious film a second batt of greater density than the first batt. The greater density second batt provides a wickability gradient for drawing fluid through the openings in the moisture-impervious film whereafter the fluid is retained in the second batt. The wickability gradient is a difference in preferential absorptivity particularly as to time wherein the more dense the absorbent batt the more liquid is drawn to the densified area. The wickability gradient is discussed more fully later. The wickability gradient may be formed by a continuous, paper-like, densified, highly compacted skin portion disposed on the surface of the second batt on the side away from the film. In the instance of a disposable diaper, the densified skin portion provides a wickability gradient to draw urine from the first batt through the perforated film and the loosely compacted batt portion of the second batt, and ultimately into the densified layer of the second batt. When the densified skin portion of the second batt becomes saturated, the excess urine flows back and is absorbed within the loosely compacted batt portion of the second batt. The moisture-impervious perforated film provides an effective barrier that prevents urine absorbed in the second batt from flowing back into the first batt or into the facing layer.

In a preferred embodiment, the absorbent panel is assembled by initially sandwiching the unperforated impervious film between the two absorbent batts, and then perforating the sandwich structure which causes fibers from one batt to extend through the perforations and into the other batt. This creates a conduit that channels urine from one batt into the other batt.

BRIEF DESCRIPTION OF THE DRAWINGS

FIG. 1 is a perspective view, with portions broken away for clarity of illustration, of an open unfolded diaper of the present invention;

FIG. 2 is an enlarged cross-sectional view through one of the marginal side portions of the diaper illustrated in FIG. 1;

FIG. 3 is an enlarged cross-sectional detail view of an absorbent panel of a modified form of an embodiment of the present invention;

FIG. 4 is a perspective view on a reduced scale of a diaper in accordance with the present invention in its configuration after being put on an infant; and FIG. 5 is an enlarged cross-sectional view through one of the marginal side portions of a diaper of modified form of an embodiment of the present invention.

DETAILED DESCRIPTION OF THE INVENTION

Referring to FIGS. 1 and 2 of the drawings, the diaper assembly 10, when fully opened and laid out flat, comprises a lowermost moisture-impervious backing sheet 12 which is rectangular in shape, a highly moisture-absorbent fibrous pad, or panel 14, which is also rectangular in shape, but smaller than the impervious backing and centrally disposed thereon, and an overlying facing layer 16 of fibrous material, which is also rectangular in shape, equal in dimension, and coterminous with the impervious backing and in contact therewith in the marginal portions of the diaper extending peripherally beyond the absorbent pad, i.e., in the portions 16b and 12b of the facing layer 16 and the impervious backing 12, respectively.

The panel 14 includes a first loosely compacted, cellulosic fibrous batt 15 and a second cellulosic fibrous batt 17 of greater density separated from the batt 15 by a moisture-impervious film 20 having a plurality of perforations 21 therein. The batt 17 includes a loosely compacted batt portion 19 positioned in a face-to-face underlying relationship with respect to the perforated sheet 20. Integral with the batt is a paper-like densified highly compacted lowermost fibrous layer 18, which is adhered to the impervious backing sheet 12 by bead lines of adhesive 22 substantially throughout the interface therebetween. Marginal portion 16b and 12b are also adhered to each other by bead lines of adhesive 22.

In a preferred embodiment of the invention, a moisture-impervious sheet 12 is formed of polyethylene having a thickness of approximately 0.001 inch. The sheet may be smooth, or may be embossed to improve its drape and feel. Other suitable flexible moisture-impervious sheets may be used in accordance with the invention, such as, for example, polyethylene terephthalate sheets having a thickness of about 0.005 inch.

The moisture-impervious sheet 20 may also be formed of polyethylene having a thickness of approximately 0.0005–0.0025 inch. Like the backing sheet 12, the moisture-impervious sheet 20 may be smooth, or may be embossed to improve the drape of the diaper. A large number of small perforations 21 are provided in the sheet 20, and the perforations may have a diameter from between about 0.05 to about 0.3 inch, and most preferably from between about 0.1 to about 0.2 inch. The above dimensions are given for purpose of example, it being understood that the perforations 21 must be sufficiently large in size to enable the wickability gradient provided by the densified portion 18 of the batt 17 to readily draw urine present in the batt 15 through the film 20. Furthermore, the perforations 21 must be sufficiently small in size that once urine is absorbed in the batt 17, the film 20 will function as an effective barrier preventing the urine from flowing back into the batt 15. The perforations are preferably separated from one another by about 0.5 inch or more or less, and may be arranged in a regular geometric pattern, as illustrated in FIG. 1, or they may also be arranged so as to concentrate the number of openings in a limited area such as the central area.

The moisture-impervious sheet 20 may be preformed and cut and merely laid in place between the first and second batts in the absorbent panel. Alternatively, the moisture-impervious film 20 may be extruded onto the cellulosic batt in such a way that the openings are formed immediately or it may be extruded as a solid film which is later perforated.

The batts 15 and 17 are formed of loosely compacted short cellulose fibers, such as wood pulp fibers, or cotton linters, or mixtures thereof, which are primarily held together by interfiber bonds requiring no added adhesive, as is known in the art. Briefly, these batts are a low bulk density coherent web of loosely compacted cellulose fibers preferably comminuted wood pulp fibers in the form of so-called "fluff".

The term "short fibers", as used herein, refers to fibers less than about ¼ inch in length, in contrast to "long fibers", or "textile length fibers" which are longer than about ¼ inch in length and generally are between about ½ and 2½ inches in length.

The paper-like densified layer 18 of the batt 17 is formed by a slight moistening of one surface of the batt followed by the application of pressure thereto. The nature of the batt and of its densified layer and the method of producing the same are described in U.S. Pat. No. 3,017,304, dated Jan. 16, 1962.

The composite density of the panel 14, including the batts 15 and 17, should be above about 0.07 grams per cubic centimeter, and preferably between about 0.1 and 0.15 grams per cubic centimeter. The foregoing density values are applicable to the diaper as produced. In storage and handling, the loft or thickness of the batt is increased to some extent, resulting in lowered densities.

The facing layer 16 is made up of a mixture of fibers consisting predominantly of short cellulosic fibers such as wood pulp fibers or cotton linters. The short fibers in the facing layer are in uniform admixture with 2 to 25% by weight of textile length fibers, such as rayon fibers uniformly cut to 1½ inch length. The short and long fibers are randomly and substantially uniformly dispersed and bonded with a bonding agent such as a self-crosslinking acrylic emulsion. The facing web also may be treated with a wetting agent to partially counteract the water-repellency of the bonding agent and bring the facing layer to the desired degree of wettability.

It is highly desirable to provide for selective wettability among the above-described fibrous components of the diaper, such that the moisture is selectively drawn from the facing layer 16 into the first batt 15, from the first batt 15 through the perforated film 20 and into the batt portion 19 on the second batt 17, and finally into the densified layer 18 of the second batt 17.

The least wettable of the fibrous elements of the diaper of the present invention is the facing layer. However, even in the facing layer, the ability to be wetted by water is desired. Water repellency in the facing layer is not desired since, at the desired fiber densities in the facing layer, water repellency can prevent the liquid from penetrating into the facing layer and the absorbent layers behind it. For this reason, the facing layer is usually treated with a wetting agent, such as an anionic surfactant, to moderate and reduce the water repellency which may be imparted to the short and long fibers of the web by the bonding agent which bonds them into an integral layer. After treating with a wetting agent, the facing layer is receptive to penetration by urine, but remains less wettable than the batt.

A useful parameter of wettability is the liquid-fiber contact angle for the individual fibers of the layer, the contact angle approaching 90° for fibers which are difficultly wettable, exceeding 90° for fibers which are highly water repellent, and approaching 0 for fibers which are wettable by water.

In any particular facing layer, the liquid-fiber contact angle for individual fibers may vary considerably because of unevenness of distribution of the water repellent bonding agent and unevenness of distribution of wetting agent. Nevertheless, a liquid-fiber contact angle between about 30° and about 60° for more of the individual fibers in a random selection provides suitable wettability in the facing layer, and a liquid-fiber contact angle between about 40° and about 60° is preferable.

The body of the batt is substantially more wettable than the facing layer and tends to draw liquid away from the facing layer. The individual fibers of the batt are extremely wettable, generally having liquid-fiber contact angles below about 15° and approaching 0 in the optimum embodiment. The wickability, or preferential absorptivity of the body of the batt for water is limited, however, by its low density which results in a large effective capillary radius for the capillaries between adjacent fibers.

The pressure causing a liquid to enter a cylindrical capillary is expressed by equation:

$$P = (2\gamma \cos \theta / r)$$

where
P is the capillary pressure,
$\gamma$ is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is 0), and increases with narrower capillary radii so that narrower capillaries will draw liquid from wider ones.

The relative wickability between the facing layer and the body of the batt is affected by both the relative densities of the layers and the relative wettability of the individual fibers in each layer. The facing layer is sometimes more dense than the body of the batt, tending to provide greater wickability in the facing layer, but even then the individual fibers of the batt have substantially smaller liquid-fiber contact angles than those of the facing layer, overcoming the density difference and providing a substantial overall increase in capillary pressure to absorb liquid into the body of the batt.

The densified fiber layer 18 (FIG. 2) of the batt 17 provides the maximum capillary pressure because it combines the very low contact angle of the fibers of the batt 17 with the high density (small capillary radius) of the densified fibers. Thus, the densified layer 18 provides a wickability gradient for drawing urine from the batt 15 through the perforated film 20, and through the batt portion 19 of the batt 17 into the densified skin layer.

When urine is voided into an area of the facing layer, it partially wets the facing layer and is absorbed therein, spreading out to a limited extent to form a roughly circular wetted zone therein. When the urine passes through the facing layer and comes into contact with the body of the first batt, it is preferentially absorbed into the body of the batt because of the enhanced wettability thereof. It spreads within the body of the batt to wet a larger, roughly circular zone therein. When the urine passes through the perforated film and into the second batt, it spreads out slightly larger than the zone wetted in the first batt. When the urine is drawn through the second batt and into contact with the densified layer, it is strongly drawn therein because of the high density of the densified layer and is spread laterally through a much larger substantially circular zone, or even to the edges of the densified layer depending on the amount of urine passed.

On occassion when a substantial amount of urine has been voided, the densified layer becomes saturated and excess urine, aided by the presence of the impervious backing sheet and its adherence to the densified layer in a discontinuous pattern substantially throughout the interface therebetween, flows into the previously dry portions of the low density area of the second batt. The film provides a barrier which traps the urine in the second batt to insure that the facing layer remains dry.

The densified layer of the second batt, for the reasons explained above, creates a high capillary pressure which tends to move liquid away rapidly from the area of the original wetting. However, the speed of liquid migration is limited in the densified layer because of the resistance provided by its small capillaries. The second batt with its densified layer in intimate contact with absorbent material of lesser density, provides improved speed of liquid migration over either the densified layer alone, or the uncompressed layer alone.

While it is not desired to be bound by any particular theory of operation, it is believed that the improvement in speed of liquid migration obtained by the cooperation of the dense layer and uncompressed layer of the second batt results from the proximity of the two layers and the fact that just adjacent to the high capillary pressure generated by the dense layer are the large capillaries of the uncompressed layer which can move larger quantities of the liquid with relatively little flow resistance.

There is also cooperation between the densified layer of the second batt and the impervious sheet to which it preferably is adhered. A voiding of urine usually takes place within a short time, and the rate of absorption of the diaper might be overwhelmed during this short period in spite of the diaper's ultimate capacity to absorb the amount of liquid voided and in spite of the relatively high rate of absorption obtainable for the reasons specified above. The impervious sheet serves to hold the urine and keep it from wetting the bed clothes or outer clothing so that the absorptive portions of the diaper can have the time to function. In addition, the impervious sheet serves as an anchor to stabilize the fluff portion of the second batt against migration of the loosely compacted fibers, since the impervious sheet is adhered to the densified layer integral with the fluff portion of the second batt, over a widely distributed area.

The perforated film allows migration of the urine from the first batt, which initially receives the urine, to the denser second batt below. Also, the perforated film serves to retain the urine that has migrated to the second batt, in the region of the second batt, thus preventing the urine from seeping upward to the facing layer. Therefore there is less wet-back to the skin of the wearer and the facing remains substantially dry.

In another embodiment of the present invention in FIG. 5, a second densified layer is provided immediately below the perforated film. Referring to FIG. 5, the diaper has a moisture-impervious backing 50 on one side of an absorbent panel 52 and an overlying facing layer 54 on the other side. The panel 52 includes a first loosely compacted, cellulosic fibrous batt 56 and a second cellulosic fibrous batt 58 of greater density separated from the batt 56 by a moisture-impervious film 60 having a plurality of perforations 62 therein. The batt 58 includes a loosely compacted batt portion 64 sandwiched between densified fibrous layers 66 and 68. The densified fibrous layer 66 provides a wickability gradient to assist in drawing the urine through the perforations 62 in the moisture-impervious film 60. As the loosely compacted batt portion 64 becomes wet, the lower densified layer 68 draws the urine from the loosely compacted batt portion 64, and spreads it laterally through the densified layer.

It may be noted that preferably the facing layer as assembled into the diaper (whether folded or not) is coterminous with the impervious sheet and there is no folding over of the impervious sheet to envelop any edge of fibrous material. Thus, there is no portion of the upper surface of the diaper which is covered with any plastic material, and no plastic material comes into direct contact with the infant's skin when the diaper is affixed in position by pins or tabs. Prolonged direct contact of plastic material with an infant's skin can cause irritation and infection but, nonetheless, is employed in prior art disposable diapers to provide an impervious seal to the infant's skin. The superior absorptive capacity of the diaper of the present invention and its superior functioning makes such plastic-to-skin contact unnecessary.

The diaper of the present invention is normally packaged and sold in a folded condition. For example in FIG. 2, the side margins 12b and 16b of the impervious sheet 12 and the facing web 16, together with a portion of the panel 14 are folded inwardly in a first fold to provide as the uppermost layer of the fold, a portion of the moisture-impervious sheet. This sub-assembly is then folded outwardly along each edge in a second fold to cover the first folded portion and to expose the edge portion of the facing web as the upper layer of the double fold. In the preferred embodiment, each double fold at the edge of the diaper comprises approximately one third of the resulting transverse dimension of the folded diaper, leaving approximately one third of the weight of the folded diaper as a central unfolded and uncovered portion.

The diaper is held in its folded condition by two small central spots of adhesive applied between the main body of the diaper and the overlying sides of the facing web, one spot on each folded side of the diaper. When the diaper is to be put on the infant, the folds are opened on one side of each of the adhesive spots, and the open portion of the diaper is put under the infant's buttocks while the folded portion is raised into the crotch region. The final form of the diaper is shown in perspective on a reduced scale in FIG. 4, wherein the impervious sheet 40 is placed intermediate the absorbent panel 42 which panel is covered with a facing layer 44, the adhesive tabs 46 hold the diaper securely about the infant.

In one form of the present invention, the diaper is provided with adhesive tabs 46, each having a fixed end secured to the impervious sheet 40 and a free end wherein the adhesive surface is covered with a facing sheet. The facing sheets are removed to expose the adhesive surfaces when the diaper is applied to the infant, as in the configuration shown in FIG. 4, and the free ends of the adhesive tabs are secured to opposite corners of the diaper.

In the embodiments discussed above, the second batt is denser than the first batt. One method of achieving the higher density in the second batt is to provide the densified layer discussed above. Another method is the use of a material possessing a higher density such as peat moss, thermomechanical wood pulp and the like. Still another method is densifying by other methods such as creping, embossing, overall compaction and the like.

In a preferred embodiment as shown in FIG. 3, the absorbent panel 29 of the present invention is produced by sandwiching an unperforated film between the first and second batts 30 and 32, respectively, and moving a multi-pronged perforating member through the sandwich assembly to force the prongs through the batt 30 and through the film 34 to form the perforations 36. By forming the panel 29 in this manner, a portion of the individual fibers 30' are forced through the perforations 36 and into the loosely compacted portion of the batt 32. The fibers 30', in effect, form wicks or conduits which channel urine from the batt 30 through the perforations 36 and into the loosely compacted portion of the batt 32. As is also shown in FIG. 3, when the perforations are formed an annular lip 35 is formed from the sheet 34 around each perforation 36. These lips 35 may assist in lending stability to the batt surrounding them. Furthermore, the fibers sticking through the perforations lend stability to the batt 30 and perhaps to the batt 32.

A preferred facing layer, as previously described above, contains between 75% and 98% by weight of short fibers, not exceeding about ¼ inch in length. The average short fibers are from about 1/16 to about 3/16 inch in length. The facing layer is prepared by first forming a web of randomly laid dry fibers of the desired mix of short and long lengths, the web having a density from about 0.09 grams per cubic centimeter to about 0.025 grams per cubic centimeter measured by ASTM method D-1777 at 0.16 pounds per square inch. The facing is either pre-cut and assembled with the rest of the diaper or the web is fed to a diaper assembly machine continuously and laid over the backing and superposed panel after which the facing is cut to size and assembled with the diaper.

Facing layers having weights between about 1 and about 5 ounces per square yard are generally suitable for use in the present invention. One particular facing layer which has been used with satisfaction is composed of approximately 15% textile-length fibers such as uniformly cut 1½ inch 1.5 denier rayon fibers and 85% fibers of individualized second cut cotton linters. Other suitable facing layers are made of an apertured, nonwoven fabric such as those of commonly assigned U.S. Pat. Nos. 2,862,251; 3,081,514 and 3,081,515. In addition, polyester fiber webs, polyolefin spunbonded webs and the like can be used.

When preparing a diaper in accordance with the present invention, it is preferred to adhere the impervious backing layer to the densified layer, continuously or discontinuously, over substantially the entire interface between them so as to prevent substantial separation between the two resulting in the creation of spaces in which substantial amounts of free liquid urine can accumulate. The adherence of the impervious backing layer to the paper-like densified cellulosic layer effects a dimensional stabilization of the densified layer against transverse movement and thereby brings about a stabilization of the loosely compacted fiber fluff portion 19 of the batt layer 17 since the paper-like densified layer 18 is integral with the fluff portion. In addition holding forces are transmitted from the dimensionally stable impervious backing layer through the widely distributed adhesive, to the densified layer, and thence to the fluff.

It will be understood by those skilled in the art that variations and modifications of the specific embodiments described above may be employed without departing from the scope of the invention as defined in the appended claims.

I claim:

1. An absorbent article of manufacture having a multilayer absorbent pad means, a moisture-impervious backing sheet on one side of the absorbent pad means, and a moisture-permeable facing sheet overlying the other side of the absorbent pad means, the absorbent pad means comprising a first highly-porous, loosely-compacted cellulosic fibrous batt having on one side the facing sheet and on the other side a moisture-impervious film having a plurality of openings therein for permitting fluid to pass therethrough, and on the other side of the moisture-impervious film between the film and backing sheet a second batt of greater density than the first batt to provide a wickability gradient for drawing fluid through the openings in the moisture-impervious film and retaining the fluid in the second batt.

2. The absorbent article of manufacture of claim 1 wherein the greater density of the second batt is provided by a paper-like, densified compacted cellulosic fibrous layer of relatively high wettability and relatively high fluid retentivity integral with a batt portion of the second batt on the face thereof in contact with the backing sheet.

3. The absorbent article of manufacture of claim 2 wherein said densified, highly compacted layer is a continuous layer covering the entire surface of the second batt.

4. The absorbent article of manufacture of claim 1 wherein the greater density of the second batt is provided by a paper-like, densified compacted cellulosic fibrous layer of relatively high wettability and relatively high fluid retentivity integral with a batt portion of the second batt on the face thereof in contact with the moisture-impervious film having a plurality of openings.

5. The absorbent article of manufacture of claim 4 wherein said densified, highly compacted layer is a continuous layer covering the entire surface of the second batt.

6. The absorbent article of manufacture of claim 1 wherein some of the fibers of the first batt extend downwardly through the openings in the moisture-impervious film and into the loosely compacted batt of the second batt.

7. The absorbent article of manufacture of claim 1 in which a generally annularly shaped lip surrounds each opening in the moisture-impervious film and extends downwardly into the loosely compacted portion of the second batt.

8. The absorbent article of manufacture of claim 1 in which a generally annularly shaped lip surrounds each opening in the moisture-impervious film and extends downwardly into the loosely compacted portion of the second batt and wherein some of the fibers of the first batt extend downwardly through the openings and into the loosely compacted portion of the second batt.

9. The absorbent article of manufacture of claim 1 in the form of a diaper wherein the backing sheet and the facing layer are substantially rectangular and substantially coextensive, the absorbent panel is substantially rectangular, narrower than the backing sheet and the facing layer, and centrally disposed with respect thereto to provide marginal portions of the diaper in which the backing sheet and the facing layer are in direct contact with each other.

10. The absorbent article of manufacture in the form of a diaper of claim 9 wherein the fibers of the facing layer are bonded together by a water-repellent polymeric bonding agent and wherein the fibers of the facing layer are coated with a surfactant.

11. A multi-layer diaper comprising: a generally rectangularly shaped layer in the form of a water-wettable bonded web of mixed short and long fibers as a facing layer; an absorbent panel including a first highly porous loosely compacted, cellulosic fibrous batt underlying the facing layer and having greater wettability to water than the facing layer, the first batt being generally rectangularly shaped and smaller than the facing layer; a water-impervious film underlying the first batt, the film having a plurality of openings therein for permitting fluid to pass therethrough in the form of perforations; and a second batt including a highly porous, loosely compacted, cellulosic fibrous batt underlying the perforated film, the second batt further including a paper-like, densified compacted, cellulosic layer of relatively high wettability and relatively high fluid retentivity integral with the loosely compacted batt portion of the second batt on the face thereof opposite the face in contact with the perforated film to provide a wickability gradient for drawing fluid through the perforated film and trapping fluid in the second batt, the film and first and second batts being of substantially the same size and coextensive with one another; and a water-impervious backing sheet adhered to the face of the second batt opposite the face in contact with the perforated film, the water-impervious sheet being of substantially the same size as the facing layer and being adhered thereto in the marginal regions lying beyond the regions of the absorbent panel.

12. The diaper of claim 11 wherein some of the fibers of the first batt extend downwardly through the perforations and into the loosely compacted batt of the second batt.

13. The diaper of claim 11 in which a generally annularly shaped lip surrounds each perforation and extends downwardly into the loosely compacted portion of the second batt.

14. The diaper of claim 11 in which a generally annularly shaped lip surrounds each perforation and extends downwardly into the loosely compacted portion of the second batt and wherein some of the fibers of the first batt extend downwardly through the perforations and into the loosely compacted batt of the second batt.

* * * * *